United States Patent [19]

Mayer

[11] Patent Number: 5,825,502
[45] Date of Patent: Oct. 20, 1998

[54] DEVICE FOR CLOSE-UP PHOTOGRAPHY OF SURFACES

[75] Inventor: Rolf Mayer, Griesbach, Germany

[73] Assignee: Teach Screen Software GmbH, Griesbach, Germany

[21] Appl. No.: 728,524

[22] Filed: Oct. 9, 1996

[51] Int. Cl.⁶ .............................. H04N 1/04; G03B 27/58; G06K 9/22
[52] U.S. Cl. ......................... 358/296; 358/473; 358/401; 358/498; 358/909.1; 355/47; 382/313
[58] Field of Search ..................................... 357/296, 400, 357/401, 471, 473, 493, 906, 909.1; 386/35, 96, 117, 118, 120, 121, 124; 355/21, 47, 52, 55, 67, 31; 396/5, 12, 13, 14, 65, 72, 77, 115, 148, 155, 267, 300, 310, 312, 373, 419, 420, 422, 424, 426, 429

[56] References Cited

U.S. PATENT DOCUMENTS

| | | | |
|---|---|---|---|
| 3,810,209 | 5/1974 | Bahnsen | 396/14 X |
| 3,906,520 | 9/1975 | Phillips | 396/267 X |
| 4,310,231 | 1/1982 | Konishi et al. | |
| 4,524,779 | 6/1985 | Brown, Jr. | 396/419 X |
| 4,691,712 | 9/1987 | Brown, Jr. | 396/419 X |
| 5,581,631 | 12/1996 | Ortyn et al. | 382/312 X |

Primary Examiner—Peter S. Wong
Assistant Examiner—Gregory J. Toatley, Jr.
Attorney, Agent, or Firm—Rothwell, Figg, Ernst & Kurz

[57] ABSTRACT

A mobile device for close-up -photography or -video-recording is so designed that it is easily useable for the investigation of surface details of an object which is particularly large and soft, for example human skin. When placed in contact with the surface of the object, then without further adjustments a sharp and greatly enlarged image is obtained. The device includes a distance-enforcing structure between the optical system and the object which in the object-side focal area ends with a vaulted surface. The vaulted surface is mechanically stiff and is shaped to compensate the image-plane curvature of the optical system by establishing a corresponding object-plane curvature. This compensation enhances the sharpness of the image obtained for an object surface which is pressed against the vaulted surface and thus is positioned in the true object-side focal area of the optical system.

12 Claims, 2 Drawing Sheets

DEVICE FOR CLOSE-UP PHOTOGRAPHY OF SURFACES

BACKGROUND OF THE INVENTION

1. Field of the Invention

The invention concerns a device that allows to record close-up images, also denoted as 'macroscopic' images, of surface details, particularly of large and flexible surfaces like human skin which are extraordinarily sharp. An embodiment preferred for medical application, particularly in dermatology, is described here. It comprises a mobile hand-operated video camera supplemented with additional components as described below.

2. Description of Related Art

The method commonly used for the investigation of skin areas with an extent of millimeters to centimeters is the direct visual observation with a hand operated 'touch-down' microscope or 'Dermatoscope' which is positioned between the eye of the observer and the skin. One of the disadvantages of this method is that the observer's face is brought near to the skin, which often is sick. Another disadvantage is that no permanent record of the observation is taken. Video cameras so far are used only with their moderately enlarging built-in optics or they are attached to table-mounted microscopes which lack mobility.

A more general problem of microscopic imaging is that the distance range over which a sharp image can be obtained is very small and consequently it is difficult to place the object within the distance-range of sharpness or 'depth of focus'. This is particularly difficult for soft, flexible surfaces and mobile operation. Further, the sharpness of the imaging is limited by the image-plane curvature of the optical system, which in reference to the object-side focal plane reduces the depth of focus.

SUMMARY OF THE INVENTION

The coupling of independent and universal optical components for the purpose of macro-photography through a zone where the light-rays which originate from an arbitrary object-point, are running parallel is already known from the patent U.S. Pat. No. 4,310,231 and is used also here. In addition to the features of said patent the device described here and in FIGS. 1–3 has the following specific advantages: The device can be placed onto surfaces of large size, for example human skin. The vaulted surface 12, which in the described embodiment is spherical convex, on the object side of the distance-enforcing tube (3) allows to position and to shape the object's soft surface in a manner that the image-plane curvature of the particular optical system is compensated. Essentially the object surface is positioned in the true, that means vaulted, object-side focal area of the optical system: the image-side focal plane then has no curvature. With other words: the image-plane curvature of the optical system is replaced by an object-plane curvature. Consequently the image sharpness is enhanced in comparison to the usual case, where the object surface is positioned in the nominal object-side focal plane.

After positioning the device onto the objects soft surface, the image is immediately sharp without further adjustments.

BRIEF DESCRIPTION OF THE DRAWINGS

The means by which the foregoing advantages and features of invention are achieved are pointed out with particularity in the claims forming the concluding portion of the specification. The invention, both as to its organization and manner of operation are described with respect to the following drawings:

DESCRIPTION OF THE PREFERRED EMBODIMENTS

Figure 1A:
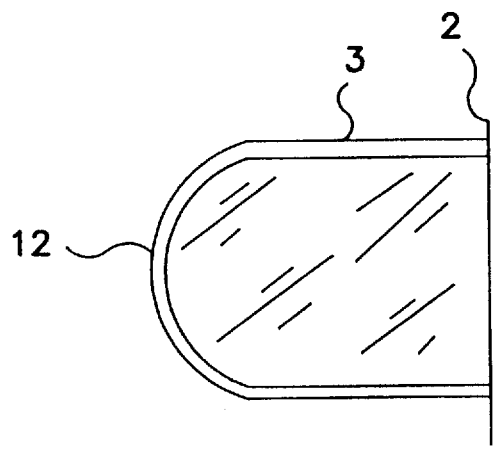
FIG. 1a is a further detail of the spherically vaulted plate which contacts the patient surface to be imaged.
Figure 1B:
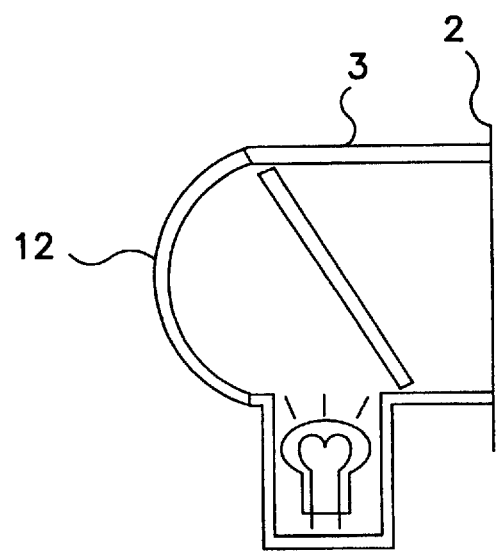
FIG. 1b illustrates an embodiment including illumination means.
Figure 1C:
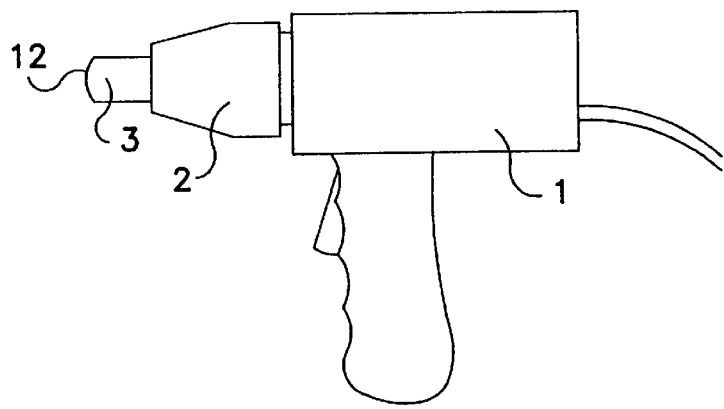
FIG. 1 is an illustration of an apparatus embodying the present invention.

FIG. 1 illustrates the basic assembly of the device: video camera with zoom optics 1, handle and trigger, additional lens system 2, distance-enforcing structure 3 with vaulted convex surface 12. FIGS. 1a and 1b both illustrate the vaulted surface 12 in cross-section, and respectively illustrate immersion fluid and illuminating means.

Figures 2A, 2B:
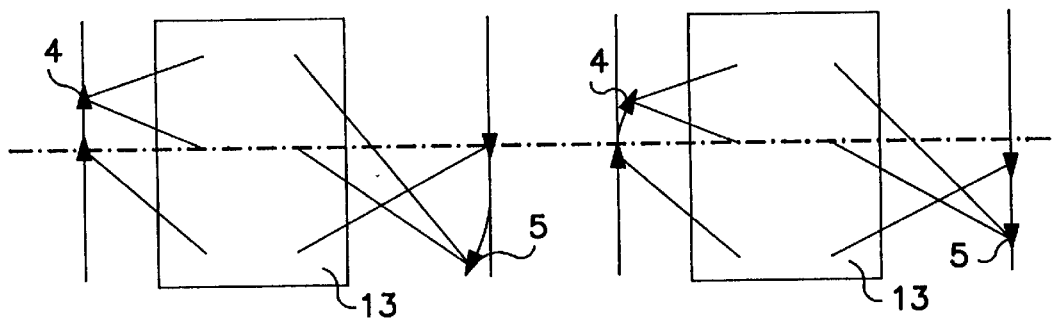
FIGS. 2a and 2b are optical schematic diagrams respectively illustrating the problem of image curvature in prior art devices and provision of an image on an image plane in the apparatus according to the present invention.

FIG. 2 illustrates the light bundles emerging from the object surface 4 which is positioned in the object focal area, passing through the lens system 2. The light rays in a bundle run in parallel 5 from the lens system 2 to the camera objective which creates a sharp picture in the camera's image plane, if adjusted for infinite object-distance.

Figure 3:
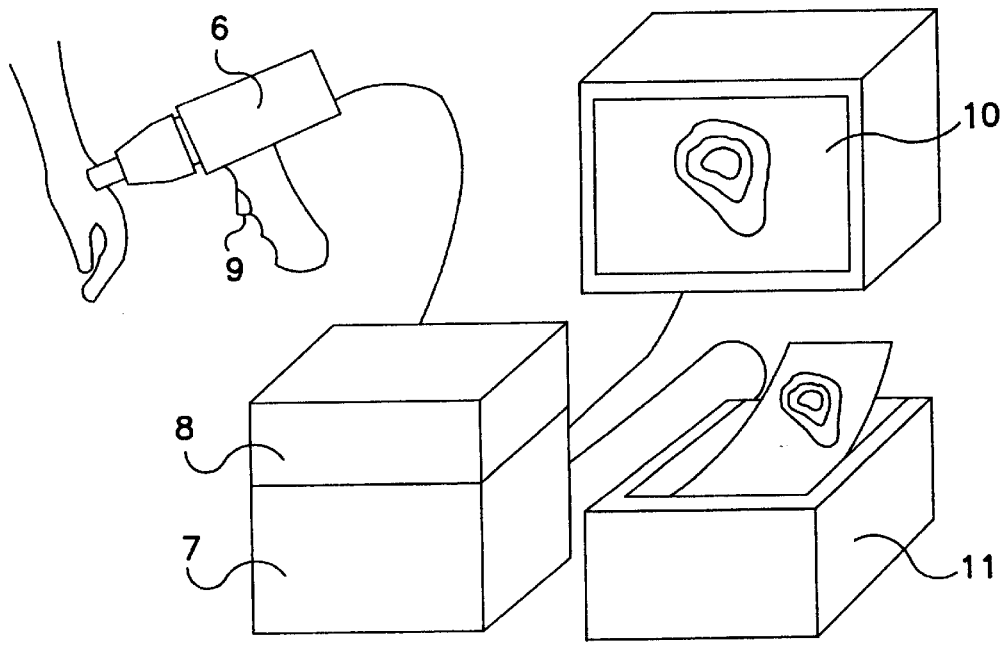
FIG. 3 illustrates use of the present invention.

FIG. 3 illustrates the usage of the assembly 6 in a system which allows to select a picture by a trigger 9, to display the picture on a screen 10 to manipulate the picture in various ways 7, to store it in a digital mass-storage means 8 and print it 11.

The distance-enforcing means is designed as a glass-tube, closed on the object side focal area by a spherically vaulted plate 12. This has several advantages: the user can visually control, viewing through the means, the process of 'touching down' the device onto the skin. This is important because the object, viewed through the camera is strongly enlarged and appears sharp only after the distance-enforcing means is already in contact with the object's surface. However, then it is inappropriate from medical reasons to move the distance-enforcing device across the sick skin area. Further, due to the fast objectives and high sensitivity of video cameras, in many cases the ambient light incident through the glass tube from the side is sufficient for recording images. In other cases the object is additionally illuminated through the side walls of the glass tube. One specific embodiment comprises several small lamps which are mounted on a ring which is attached to the housing of the lens system 2 and where the lamps focus their light through the glass walls 3 of the distance enforcing structure onto the object surface area under investigation. Further, glass allows to fulfil the hygienic requirements in medical applications most easily.

In other applications a specific illumination might be required, for example to ensure colour-correctness. In such a case an additional illumination means might be integrated into the optical system, like the embodiment which is disclosed in U.S. Pat. No. 4,310,231, or the distance enforcing means. It then is advantageous to design the walls of the distance-enforcing structure opaque to keep off ambient light.

The optical system comprises a composite lens system 2, the camera with zoom optics (1) and the distance-enforcing structure 3, 12. The built-in zoom of the video camera allows to vary the magnification factor of the optical system. The lens system 2 can be dismounted from the camera objective: the camera then also can be used with it's zoom optics alone to take images of larger areas of the skin. Between the camera objective and the lens system 2 the ray traces emerging from individual points of the object surface run parallel 5. The distance between camera objective and lens system 2 is not critical, however preferably is kept minimal. The vaulted surface 12 at the end of the distance-enforcing structure (3) is positioned in the focal plane of the lens system 2 due to the particular length of the distance-enforcing structure.

For sharp imaging the surface of the object 4 has to be positioned in close contact to the surface 12, which coincides with the optical system's object-side focal area. A properly vaulted surface 12 compensates the optical system's image-plane curvature, causing the actual image focal plane to be more flat This increases the sharpness of the image and further, for a flexible object it increases the useful distance-range or the useful 'depth of focus' over which sharp imaging is possible. So, not only soft surfaces are imaged sharper, also flexible structured surfaces can be recorded with best possible quality: the image is sharp provided the surface structure remains within the depth of focus. In such a case it can be of advantage to design the distance-enforcing means variable in length, such that the full distance range for sharp imaging can be positioned also in front of the vaulted surface 12.

The camera system is integrated into a data processing system comprising a processor 7, an electronic mass storage 8, a display screen 10, a trigger 9 for the 'still' image selection, means for text- and voice- input, for example keyboard and microphone, and a printer 11. Through this system the recorded image can be displayed, analysed, modified or amended and can be stored, possibly together with written 'text' and spoken 'voice' information, on an electronic data storage medium, i.e. a disc. The images and related information are stored and organised within a database system for later easy access and management and can be exported by electronic means or output can be produced, i.e. on a printer and loudspeaker. The 'live' or selected 'still' images can be displayed together and compared with 'archive' images retrieved from the database system.

The use of digital cameras and displays, when compared to photographic means, has the advantage that no materials are consumed. It also lacks the delays and costs intrinsic to the development of film and of enlarged paper copies. The archived digital images can be retrieved immediately anytime and no storage room for an archive of films and photographic paper copies is needed. Instead of video cameras also digital 'still' image cameras can be used.

The lens system 2 with the distance-enforcing means, when filled with an immersion fluid, could be used as an 'immersion' optics system. The magnification factor in this case increases and at the same time the distance between object 4 and lens system 2, the object-side focal length, reduces.

While specific embodiments of the invention have been described in detail to illustrate the application of the inventive principles, it will be understood that the invention may be embodied otherwise without departing from such principles.

The properties of the invention, as described in the claims and by way of example, can be of importance for the embodiment of the invention as well individually as in arbitrary combination.

I claim:

1. Device for close-up photographic or digital recording of an object surface, particularly of a soft surface on a large object, for example human skin, comprising a camera with an objective which is adjusted for infinite object distance, an additional lens system connected to the camera objective, a distance-enforcing structure connected to the lens system which ends in the object-side focal-area of the lens system with a vaulted surface and where the curvature of the surface does compensate the image-plane curvature of the optical system, thus enhancing the sharpness of the image obtained in the image-side focal plane of the camera objective, provided the object surface is placed in contact with the vaulted surface of the distance-enforcing structure.

2. Device according to claim 1, wherein the distance-enforcing structure consists of transparent material, e.g., glass.

3. Device according to claim 1, wherein the distance-enforcing structure is hollow.

4. Device according to claim 1, wherein an object illumination means is integrated in the optical system or the distance-enforcing structure.

5. Device according to claim 1, wherein the distance-enforcing structure is filled with an immersion fluid.

6. System for digital image recording of an object surface comprising a device according to claim 1, further comprising means for displaying, selecting and storing of images or sequences of images.

7. System for digital image recording of an object surface according to claim 6, further comprising one or more of the following tools: tools for comparing, modifying and analyzing the images, means for adding text information to the image datasets, tools for adding sound information to the image datasets, tools for managing the image datasets and related datasets in a database system, and means for producing output from the image- and related datasets.

8. Method for digital recording of an object surface using a system according to claim 6, comprising the selection of an image or image sequence by a trigger, the display of the images on a monitor and the storage of the images.

9. Method for digital recording of an object surface according to claim 8, comprising one or more of the following procedures: a recorded image is modified and analyzed, text is added and stored in relation with the image dataset, sound is added and stored in relation with the image dataset, the datasets containing the image and related information are stored and managed in a database system, individual "archive" images are displayed together with the recorded "live" image or other archive images for comparison, output of images and related information is produced.

10. Method for photographic or digital recording of an object surface using the device according to claim 1, comprising the step of placing the distance-enforcing structure onto the object surface so that a sharp image is obtained.

11. Method for photographic or digital recording of an object surface according to claim 8, comprising the step of visually controlling the placement of the distance-enforcing structure onto the object surface through the transparent material of the distance-enforcing structure.

12. Method for photographic or digital recording of an object surface using the device according to claim 1, comprising the illumination of the object surface through the transparent distance-enforcing structure.

* * * * *

UNITED STATES PATENT AND TRADEMARK OFFICE
CERTIFICATE OF CORRECTION

PATENT NO. : 5,825,502
DATED : October 20, 1998
INVENTOR(S) : Rolf Mayer

It is certified that error appears in the above-identified patent and that said Letters Patent is hereby corrected as shown below:

Col. 2, line 53, between "distance" and "enforcing" insert -- ---.

Col. 2, line 62, "means" should be -- structure --.

Col. 3, line 18, after "flat" insert -- . --.

Col. 4, line 7, after "system" insert -- , --.

Signed and Sealed this

Twenty-ninth Day of February, 2000

Attest:

Attesting Officer

Q. TODD DICKINSON

Commissioner of Patents and Trademarks